Figure 1:
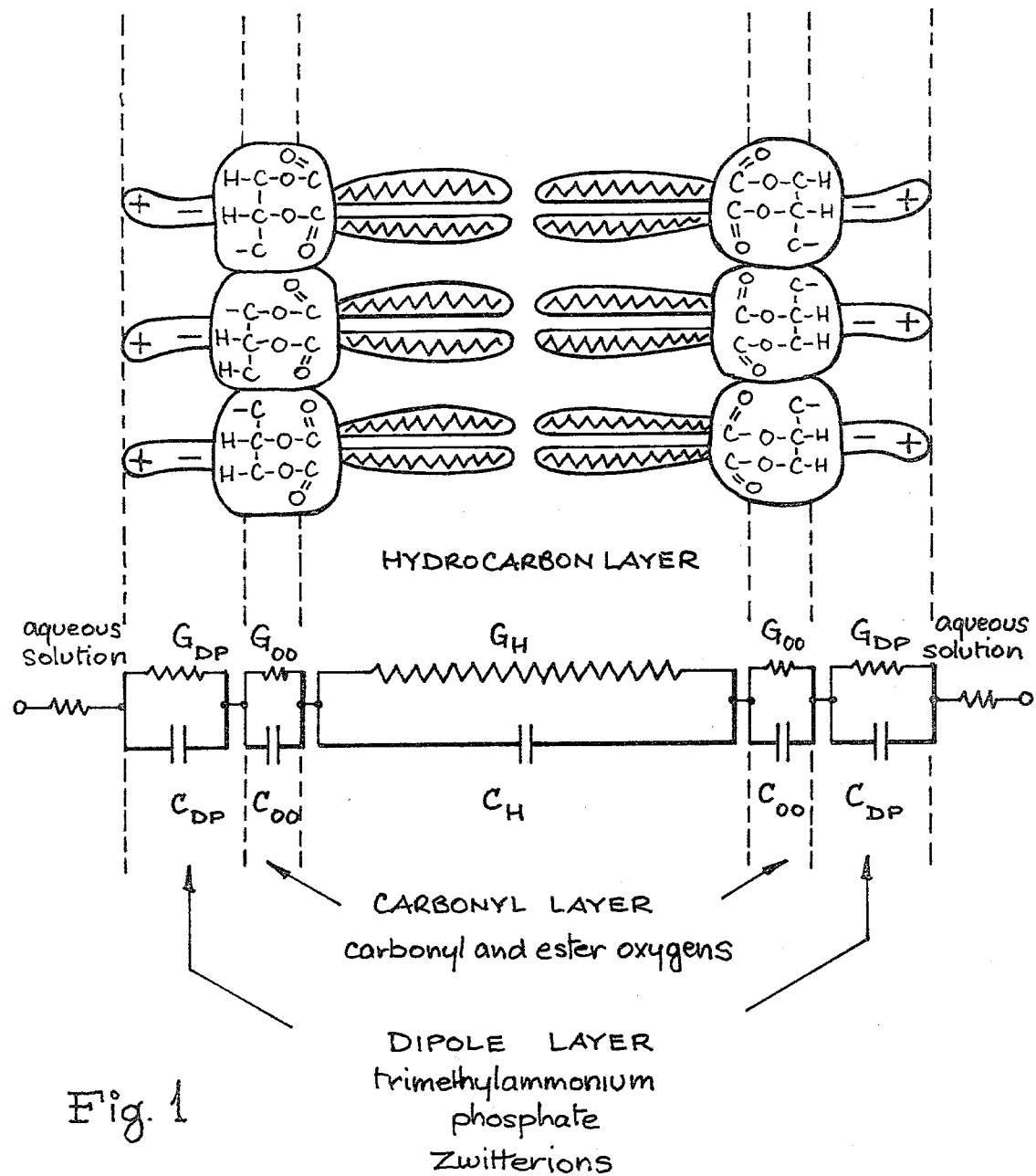

United States Patent [19]

Coster et al.

[11] 4,214,203

[45] Jul. 22, 1980

[54] LOCATION AND EFFECT OF ADSORBED CHEMICALS ON THE DIELECTRIC SUBSTRUCTURE OF MEMBRANES BY ULTRA LOW FREQUENCY SPECTROMETRY

[75] Inventors: Hans G. L. Coster, Randwick; Robert G. Ashcroft, Valcluse; John R. Smith, Coogee, all of Australia

[73] Assignee: Unisearch Limited, Kensington, Australia

[21] Appl. No.: 916,147

[22] Filed: Jun. 16, 1978

[30] Foreign Application Priority Data

Jun. 17, 1977 [AU] Australia .................................. PD475

[51] Int. Cl.$^2$ ............................................ G01N 27/42
[52] U.S. Cl. ................................................... 324/425
[58] Field of Search ........... 204/195 P, 195 M, 195 L; 324/29, 30 R

[56] References Cited

U.S. PATENT DOCUMENTS

| | | | |
|---|---|---|---|
| 3,523,066 | 8/1970 | Morris et al. | 324/29 |
| 3,661,748 | 5/1972 | Blackmer | 324/29 |
| 3,718,568 | 2/1973 | Neuwelt | 324/29 |

Primary Examiner—Michael J. Tokar

[57] ABSTRACT

Apparatus and method whereby ultra low frequency dielectric measurements allow a determination to be made of the parameters (dielectric constant, thickness and conductivity) characterizing electrically distinct layers with membranes such as bimolecular lipid or protein membranes (i.e. the major components of the membranes of living cells).

The location and effect of chemicals such as anaesthetics, tranquilizers, hormones and other substances of pharmacological and general biological interest which are adsorbed into these or other membranes can be determined. The effects of these chemicals can be quantitatively specified in terms of this effect of the substructural dielectric parameters.

5 Claims, 3 Drawing Figures

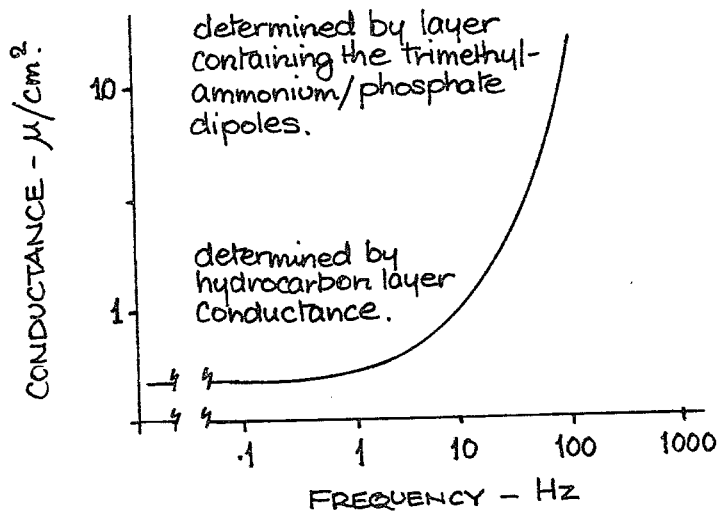
Fig. 2
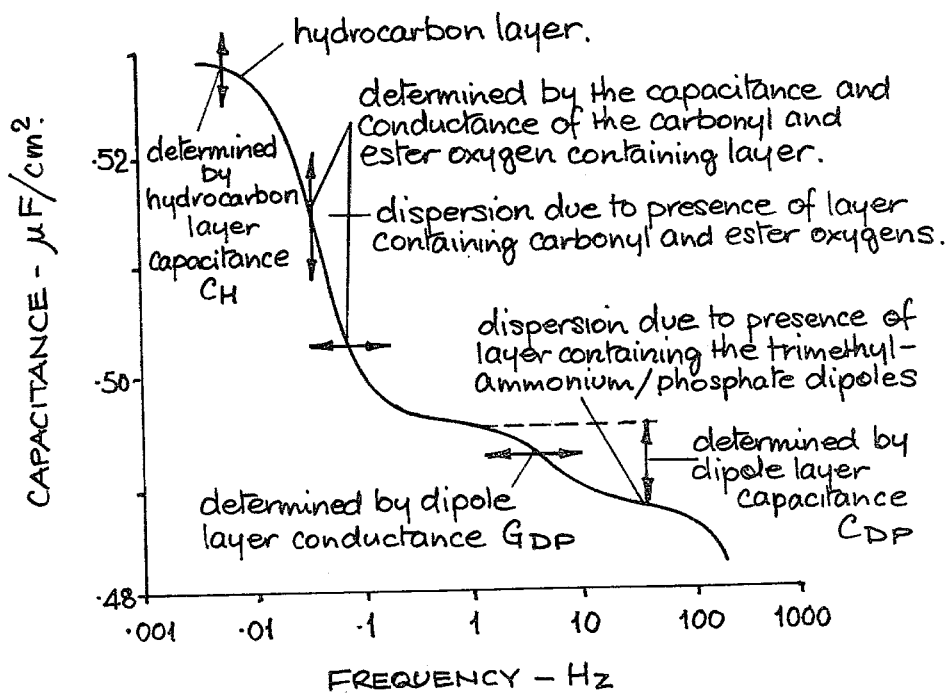

LOCATION AND EFFECT OF ADSORBED CHEMICALS ON THE DIELECTRIC SUBSTRUCTURE OF MEMBRANES BY ULTRA LOW FREQUENCY SPECTROMETRY

The present invention relates to location and effect of adsorbed chemicals on the dielectric substructure of membranes by ultra low frequency spectrometry and is based on the discovery that the presence of layers with different dielectric and/or conductance properties within membranes such as cell membranes, or membranes reconstituted from the components of cell membranes, leads to a variation with frequency of the overall capacitance and conductance. This dispersion with frequency of the capacitance and conductance of these membranes occurs over the frequency range 0.001 Hz to about 1000 Hz.

The term "membrane" includes any barrier or layer on which the chemical to be located is adsorbed and may include biological cell or tissue membranes (including membranes reconstituted from the components of cell membranes) and polymeric membranes, such as permeable, multi-layered, cellular polyamide membranes.

Measurements of the frequency dependence of the membrane capacitance and conductance over a sufficiently large frequency range at these ultra low frequencies thus allows a determination to be made of the individual dielectric and conductance parameters of those substructural layers within these membranes which have distinctly different time constants. Each such layer within the membrane will show up as a distinct feature in the dispersion curves of capacitance and conductance with frequency.

The present invention consists in apparatus for measuring and recording the variation with frequency of the overall capacitance and conductance of a membrane, such as a bimolecular lipid or protein membrane, at a plurality of frequencies within the frequency range 0.001 Hz to about 1000 Hz, comprising means for supporting such a membrane in an electrolyte, electrodes in said electrolyte whereby an alternating current may be passed through the membrane, means for generating an alternating voltage at any desired frequency within said range and applying same to said electrodes, means for measuring the overall conductance and capacitance of the membrane at each of a plurality of frequencies in the said range and of recording same.

The present invention further consists in a method of measuring and recording the variation with frequency of the overall capacitance and conductance of a membrane such as a bimolecular lipid or protein membrane, at a plurality of frequencies within the frequency range 0.001 Hz to about 1000 Hz, comprising forming a membrane of a desired composition, sequentially passing an alternating electric current at each of a plurality of frequencies within the said range through said membrane while immersed in an electrolyte, measuring the overall conductance and capacitance of the membrane at each of said frequencies and recording same. In the further application of the method a substance the effect of which is to be examined is incorporated in the membrane by introducing it into the electrolyte or, where appropriate, in the mixture from which the membrane is generated.

Figure 3:
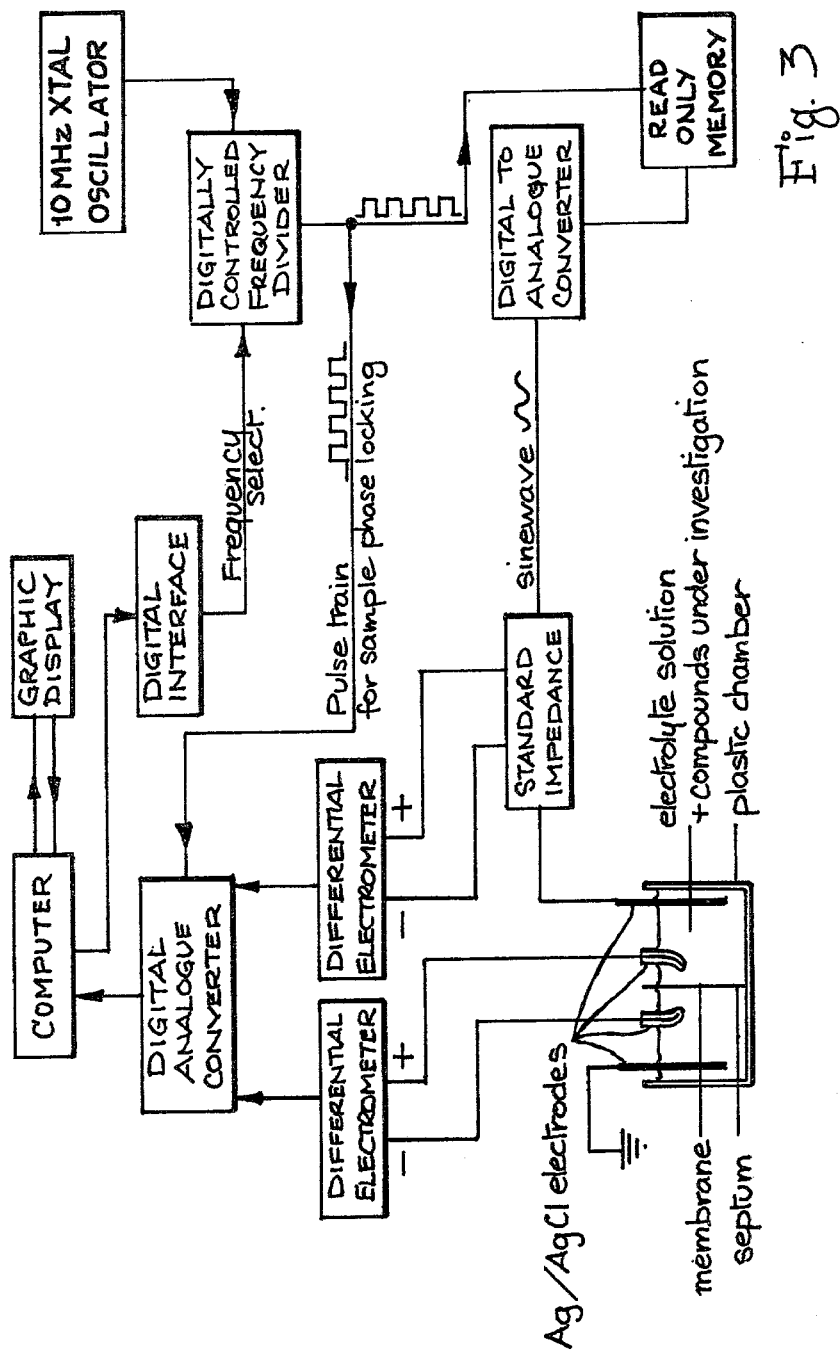

In order that the invention may be better understood and put into practice a preferred form thereof is hereinafter described by way of example with reference to the accompanying drawings in which:

FIG. 1 is a simplified schematic structure of a bimolecular lipid membrane;

FIG. 2 shows curves illustrating the frequency dependance of the conductance and capacitance of such a membrane, and is applicable to a lecithin/cholesterol membrane formed in 1 mM KCl with no other chemicals present. Some additives so change $G_H$ (and $C_H$) that the role of the carbonyl and ester oxygen region and the hydro carbon regions in this diagram are reversed; and FIG. 3 is a block diagram illustrating a form of apparatus according to the invention.

As an example of the application of the invention consider a bilayer of phosphatidyl choline (lecithin)—a common phospholipid found in cell membranes (phospholipids are a major constituent of cell membranes). A simplified, schematic, structure of such a membrane is shown in FIG. (1), together with the equivalent electrical circuit for the various distinct layers within this membrane. The frequency dependence of the capacitance and conductance of such a membrane in an aqueous solution of 1 mM KCl is shown in FIG. (2). The manner in which the various parameters of the individual layers affect the various features of these dispersion curves is indicated on the diagram.

Measurement of the changes that occur in the dispersion curves when chemicals are adsorbed into the membrane make it possible to determine which of the substructural layer(s) is affected by the adsorption of the chemical compound. The specific changes in the dielectric and conductance parameters of the layer(s) affected allow a further characterisation of the action of that chemical compound. For example, when the local anaesthetic benzyl alcohol is present in the external solution, the adsorption of this compound into the membrane leads to a decrease in the hydrocarbon region capacitance, $C_H$, if the external solution has a low salt concentration (for instance 1 mM KCl) (indicating an increase in the thickness of this layer), and also an increase in the electrical conductance, $G_H$, of this layer.

When the commonly used anaesthetic procaine is present in the solution, the hydrocarbon region capacitance increases (indicating a decrease in the thickness of this layer). Procaine also decreases the carbonyl-oxygen region capacitance.

Small differences in the structure of compounds belonging to given classes are reflected in corresponding differences in the characteristic effects which that class of compounds have on the substructure of the membrane. Thus, for instance, benzocaine, a local anaesthetic closely related to procaine, has similar effects on the substructure but its effect on the hydro-carbon layer is smaller than the effect of procaine.

It is considered that the procedure of ultra low frequency spectrometry described could be of great significance to the pharmaceutical industry because:

(1) With it, it is possible to specify the effects of chemical reagents in membranes which are closely related to the membranes of living cells.

(2) It allows a comparison to be made, of these effects, between different chemical compounds (homologues or otherwise). This would expedite the search for new substances with totally new or counteracting or potentiating effects or possessing other desirable pharmacological properties.

(3) The method allows the effects on the membrane substructural layers of new drugs to be compared to known, effective and clinically used compounds. This will expedite the testing and clinical introduction of the new drugs.

The apparatus and method of the present invention is particularly suitable to the "fingerprinting" of drugs in body cells or tissues. For example, in the case of an unconscious patient in a hospital, unable to confirm whether or not he has taken any drug or chemical substance prior to losing consciousness, it would be possible to take a blood sample, spin the cells down onto a "Milipore" filter and to test for the presence of drugs or other chemical substance in accordance with the method and apparatus of the present invention.

A further use of the present invention, used in the opposite sense, would be to test the effect of, or the reaction to a particular chemical or drug, i.e. to see whether or not a certain chemical or drug produces an adverse reaction or otherwise with a patient's cells e.g. certain antibiotics depend on certain lipids being present, and it would be possible to carry out appropriate tests in this regard, in accordance with the present invention.

The dispersion in capacitance and conductance with frequency occurs at ultra low frequencies 0.001–1000 Hz. This frequency domain has, for technological reasons, not been explored to any great extent with these membranes until the work leading to the present invention. It is for this reason, presumably, that this method of locating, and determining the effects of, chemical compounds adsorbed into these membranes has not been previously suggested.

MEMBRANE MATERIALS AND METHODS (i) General Outline

The membranes are formed across a hole in a plastic septum which divides a plastic (e.g. "Perspex" or "Plexiglass") chamber into two compartments. The compartments are filled with electrolyte solutions (e.g. KCl or NaCl etc.) to which the reagents of interest are added.

The hole in the Septum is submerged, so that when the membrane is formed it separates the electrolyte phases. Current passed from electrodes at the ends of these two compartments of the chamber thus passes through the membrane. The potential drop across the membrane is picked up by two other electrodes (insulated except at their tips) located in the electrolyte on each side of, and very close to, the membrane.

(ii) Chambers

Plastic (e.g. Perspex) blocks are machined to provide a chamber, fitted with silver/silver chloride (Ag/AgCl) electrodes for current and voltage (the latter being insulated except at the tip), then bolted together so that they sandwich a thin plastic septum having a 1.5 to 2.0 mm hole in its lower half.

(iii) Electrolyte

The solutions used to fill the cell are of KCl at concentrations between 1 and 1000 mM. Other electrolyte solutions can also be used if so desired. The reagent(s) of interest are added to the electrolyte at the desired concentration.

(iv) Membrane Solutions

The most common solution we have used for making the membranes is a n-tetradecane as solvent saturated with the appropriate phospholipid(s) (e.g. lecithin, oxidised cholesterol, or mixed lipid fractions extracted from the membranes or particular cells or organelles, e.g. mitochondrial lipids, human erythrocyte membrane lipids etc.). Reagents of interest could also be added to this solution.

(v) Membrane Formation

Three techniques are used for depositing the lipid solution across the hole. (a) A quantity of lipid solution is taken up by the remaining few hairs of a finely trimmed sable hair brush, and painted across the hole. (b) Syringe technique. Several microliters of lipid solution are deposited over the hole, and the membrane forms from the deposited film.

In both these cases a bi-molecular membrane forms spontaneously from the thick film initially deposited across the hole in the septum. (c) The bilayer is generated by the opposition of two monolayers. These monolayers are formed on aqueous solutions whose surfaces are initally below the hole in the septum. The monolayers are brought into opposition by raising the level of the aqueous solutions to above the hole in the septum.

The process of formation of the final membrane which is <10 nm (0.00001 mm) in thickness can be monitored in two ways—

(i) by optical means—the thick film reflects light but when the thickness is much less than a wavelength of visible light it appears black (i.e. very non reflecting).

(ii) by measurement of the capacitance at a fixed frequency. As the film thins the capacitance increases until the bimolecular membrane has formed, when the capacitance remains substantially constant.

ELECTRONIC APPARATUS

10 MHz square wave pulses, derived from a crystal oscillator, are fed to a digital frequency divider. The amount of frequency division is under control of the computer via its digital interface. A sine wave of the desired frequency can then be synthesised by sequentially reading a read-only-memory (preprogrammed with a sine table) into a digital to analogue converter. The frequency of this sinusoidal output can thus be varied from 0.001 Hz to 1000 Hz under computer control.

The sinusoidal current is applied to a suitable standard impedance and the membrane in series. The voltages developed across the two elements are monitored by two differential electrometer amplifiers whose outputs are sampled by the analogue-to-digital converters; the sampling is triggered by the same pulses as the one used to generate the sine wave, so that the two processes are very tightly phase-locked. Good noise rejection is achieved by sampling over several cycles, the number being computer controlled.

The data from the analogue-to-digital converters is stored in the computer memory and the data are fitted, using the computer, by the method of least squares to sinusoidal functions of the appropriate frequency.

The amplitudes and phase angles of the sine functions so determined are used to calculate the frequency-dependent capacitance and conductance of the membrane over the specified frequency range.

All the operations described are performed with the computer for a complete set of pre-specified frequencies. At the end of the measurements the complete dispersion curves are produced on the graphic display. The computer used is a small compact machine which is permanently interfaced with the other electronic devices—see FIG. 3.

Four electrodes are used in the measurement; 2 for current and 2 independent electrodes to measure the potential difference developed across the membrane. This "four-terminal" method avoids the effects otherwise introduced by the electrode-solution interface at these ultra low frequencies which can mask the dispersion-with-frequency effects in the membrane itself. Although Ag/AgCl electrodes are convenient to use at present, others are possible.

The whole unit could be fitted into a box no larger than 300 mm × 250 mm × 300 mm.

The resolution in amplitudes is 0.1% and in phase angle, 0.01°.

The system allows measurements over the frequency range 0.001 Hz to 1000 Hz.

Although the invention has been described above with reference to preferred embodiments and drawings, it will be appreciated that numerous variations, modifications or alternatives may be substituted for specifically described features without departing from the spirit or scope of the invention as broadly described.

What we claim is:

1. Apparatus for measuring and recording the variation with frequency of the overall capacitance and conductance of a membrane, such as a bimolecular lipid or protein membrane, comprising: means for supporting such a membrane in an electrolyte, first electrodes in said electrolyte for passing an alternating current through the membrane, means for generating an alternating voltage at any desired frequency of a plurality of frequencies within a range of from 0.001 Hz to about 1000 Hz and applying same to said electrodes, means for measuring the overall conductance and capacitance of the membrane at each of a plurality of frequencies in said range and for recording the same, said last-mentioned means including second electrodes separate from said first electrodes.

2. A method of measuring and recording the variation with frequency of the overall capacitance and conductance of a membrane, such as a bimolecular lipid or protein membrane, comprising: forming a membrane of a desired composition, sequentially passing an alternating electric current at each of a plurality of frequencies within a frequency range of from 0.001 Hz to about 1000 Hz through said membrane by first electrodes while said membrane is immersed in an electrolyte, measuring the overall conductance and capacitance of the membrane at each of said frequencies by means of second electrodes and recording the conductance and capacitance.

3. A method of locating and/or detecting an adsorbed chemical substance on a membrane by a method as claimed in claim 2.

4. A method of measuring the effect of an adsorbed chemical substance on a membrane by a method as claimed in claim 2.

5. An apparatus according to claim 1, wherein said measuring means includes a high impedance amplifier.

* * * * *